United States Patent [19]

Bacha et al.

[11] 4,040,911

[45] Aug. 9, 1977

[54] PROCESS FOR INHIBITING THE POLYMERIZATION OF STYRENE

[75] Inventors: John D. Bacha; Charles M. Selwitz, both of Monroeville, Pa.

[73] Assignee: Gulf Research & Development Company, Pittsburgh, Pa.

[21] Appl. No.: 646,399

[22] Filed: Jan. 2, 1976

[51] Int. Cl.$^2$ .................. B01D 3/10; C07C 15/10
[52] U.S. Cl. .......................... 203/9; 203/51; 203/91; 260/669 A
[58] Field of Search .................. 203/9, 51, 56, 65, 91; 260/669 A

[56] References Cited

U.S. PATENT DOCUMENTS

| | | | |
|---|---|---|---|
| 2,399,340 | 4/1946 | Franz | 203/9 |
| 3,448,015 | 6/1969 | Rogers | 203/9 |
| 3,632,626 | 1/1972 | Schneller | 260/669 A |
| 3,654,129 | 4/1972 | Bloch | 203/9 |

Primary Examiner—Hiram H. Bernstein

[57] ABSTRACT

The present invention relates to a process for inhibiting the polymerization of styrene monomers during the purification of crude styrene.

6 Claims, No Drawings

PROCESS FOR INHIBITING THE POLYMERIZATION OF STYRENE

FIELD OF THE INVENTION

This invention relates to a process for inhibiting the polymerization of styrene, during the purification of crude styrene, using a quinone alkide in combination with a hindered phenol as the polymerization inhibitor.

Styrene is utilized extensively in the plastics industry for the manufacture of plastics, rubber-modified impact polystyrene, butadiene-styrene terpolymer, styrene acrylonitrile copolymer and in the production of styrene-butadiene type synthetic rubber.

DESCRIPTION OF PRIOR ART

The use of styrene polymerization inhibitors in the production of styrene monomer is known. For example, most of the styrene produced today is manufactured from ethylbenzene in a continuous dehydrogenation process using either the adiabatic cracking method or the isothermal method. The two methods differ only in the manner in which the heat necessary for the conversion of ethylbenzene to styrene is supplied.

The final step in styrene manufacture is the purification of styrene in the dehydrogenation reactor effluent. Vacuum distillation is commonly used to keep toward temperatures low and to minimize the polymerization of styrene. In addition, to further reduce styrene polymerization, inhibitors such as sulfur dioxide or dinitrophenols are introduced into the purification stills. In particular, U.S. Pat. No. 3,644,549, Innes et al, issued Feb. 22, 1972 relates to the production of styrene by the dehydrogenation of ethylbenzene using a ferrite catalyst and sulfur dioxide as an inhibitor, which is then carried through the purification stages.

Government regulations and restrictions concerning the use of sulfur compounds in reactions which may pollute the atmosphere have resulted in a search for other alternatives and compounds suitable for use in styrene manufacture. Dinitrophenol has been suggested as a substitute for sulfur dioxide in the production of styrene. The compound, however, is toxic, very difficult to store and presents a fire hazard.

As can readily be determined from the foregoing, various methods and polymerization inhibitors have been employed in the production and manufacture of styrene. There is, however, a continuous and ongoing search for newer, better and more economical methods for producing styrene monomer

SUMMARY OF THE INVENTION

This invention relates to a method for inhibiting the polymerization of styrene monomer during processing thereof; the improvement which comprises a comprises a continuous mass for preparing styrene, adding during said processing a polymerizing inhibiting amount of a quinone alkide in combination with a hindered phenol, said quinone alkide having the formula:

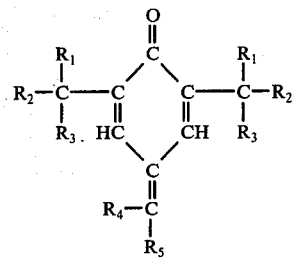

wherein $R_1$–$R_2$ and $R_3$ are either alike or different members selected from the group consisting of hydrogen, straight or branched chain alkyl moieties having from 1 to 8 carbon atoms; phenyl and alkyl substituted phenyl moieties having up to 9 carbon atoms, cyclic hydrocarbon moieties having from 3 to 5 carbon atoms; and where $R_4$ and $R_5$ are either alike or different, members selected from the group consisting of hydrogen, straight or branched chain alkyl moieties having from 1 to 18 carbon atoms, phenyl and alkyl substituted phenyl moieties having up to 9 carbon atoms, and cyclic hydrocarbon moieties having 3 to 5 carbon atoms; and said phenol having the formula:

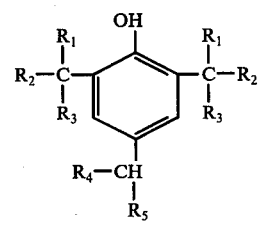

wherein $R_1$, $R_2$, $R_3$, $R_4$ and $R_5$ are defined above.

DETAILED DESCRIPTION OF PREFERRED EMBODIMENTS

The styrene purification process of the present invention can be carried out in a conventional manner, using conventional methods known in the art, with the exception that a quinone alkide in combination with a hindered phenol is added to the purification zone of crude styrene monomer during the purification step of a mass or continuous production process.

A commercial method of manufacturing styrene monomer consists of dehydrogenating ethylbenzene to styrene by contacting the ethylbenzene under dehydrogenation conditions with a catalyst. The crude styrene which contains some impurities is next passed through a pot containing sulfur, where enough sulfur is dissolved to act as a styrene polymerization inhibitor. This styrene which is diluted with ethylbenzene, tar and sulfur is transported to a purification still, containing separation trays (e.g. a single column of approximately 70 plates) and is distilled under reduced temperature and pressure. The purified styrene is recovered from the overhead while polystyrene, tars and sulfur compounds pass through the bottom portion of the distillate.

In accordance with the present invention, styrene is continuously mass produced in a dehydrogenation process of ethylbenzene in any type of reactor conventionally employed for a continuous mass styrene production process. For example, a reactor is charged with ethylbenzene under dehydrogenation conditions and crude styrene is recovered using air or water cooled or both.

Before styrene is introduced to the purification still, a minor but polymerization inhibition amount of a quinone alkide in combination with a hindered phenol substantially as described and claimed herein is charged to the purification zone. Crude styrene is then forwarded to the purification still, where the styrene is purified and concentrated by vacuum distillation to keep the still temperatures low and minimize styrene polymerization.

In particular, it is desirable to maintain the still temperature below 105° C. and a total pressure drop in the still of 315 mm Hg or less. The purification step in the mass production of styrene can be conducted according to methods commonly employed in the art. One method consists of introducing the crude styrene into towers containing distillation sieve tower trays, the concept of which is described in U.S. Pat. No. 3,282,576, Bruckert et al.

It should additionally be understood that the reaction temperature and pressure employed in the purification step of the process will fall within the range of temperatures and pressures customarily employed in the manufacture and purification of styrene monomer. For example, during the purification and concentration of styrene monomers, the purification still is normally operated at a temperature range of from about 90° C. to about 100° C. and under a vacuum of from about 160 mm Hg to about 315 mm Hg to reduce styrene polymerization and aid in the recovery of styrene monomer.

Quinone alkides which are suitable for use include 2,6-di-t-butyl-4-methenyl quinone methide; 2,6-di-t-butyl-4-ethenyl quinone methide; 2,6-di-t-butyl-4-n-propenyl quinone methide; 2,6-di-t-butyl-4-isopropenyl quinone methide; 2,6-di-t-butyl-4-n-butenyl quinone methide; 2,6-di-t-butyl-4-iso-butenyl quinone methide; 2,6-di-t-butyl-4-sec-butenyl quinone methide; 2,6-di-t-butyl-4-n-pentenyl quinone methide; 2,6-di-t-amyl-4-methenyl quinone methide; 2,6-di-t-amyl-4-ethenyl quinone methide; 2,6-di-n-dodecyl-4-methenyl quinone methide; 2,6-di-n-dodecyl-4-ethenyl quinone methide; 2,6-di-cyclopentyl4-methenyl quinone methide; 2,6-dicyclopentyl-4-ethenyl quinone methide; 2,6-dicyclohexyl-4-methenyl quinone methide; 2,6-dicyclohexyl-4-ethenyl quinone methide; or 2,6-di-phenyl-4methenyl quinone methide. The quinone alkides herein are preferably used in the purification step of the process in the amount of from about 25 ppm to about 1,000 ppm parts of styrene monomer in the purification still, preferably from about 50 ppm to 800 ppm parts of styrene monomer.

Hindered phenols which are suitable for use include 2,6-di-t-butyl-4-methyl phenol; 2,6-di-t-butyl-4-ethyl phenol; 2,6-d -butyl-4-n-propyl phenol; 2,6-di-t-butyl-4-isopropyl phenol; 2,6-di-t-butyl-4-n-butyl phenol; 2,6-di-t-butyl-4-iso-butyl phenol; 2,6-di-t-butyl-4-sec-butyl phenol; 2,6-di-t-butyl-4-n-phentyl phenol; 2,6-di-t-amyl-4-methyl phenol; 2,6-di-t-amyl-4-ethyl phenol; 2,6-di-n-dodecyl-4-methyl phenol; 2,6-di-n-dodecyl-4-ethyl phenol; 2,6-di-cyclo pentyl-4-methyl phenol; 2,6-di-cyclo pentyl-4-ethyl phenol; 2,6-di-cyclo hexyl-4-methyl phenol; 2,6-di-cyclo hexyl-4-ethyl phenol; or 2,6-di-phenyl-4-methyl phenol. Normally, the hindered phenol is present in the process from about 25 ppm to about 1,000 ppm parts of styrene monomer in the purification still, preferably from about 50 ppm to about 800 ppm parts of styrene monomer. The phenols in the instant invention are preferably in a molar ratio of phenol to quinone alkide of from about 1:10 to about 20:1 respectively.

Hindered phenols, when added to the purification zone of styrene monomers, do not inhibit the polymerization of styrene. It has surprisingly been discovered, however, that hindered phenols, in combination with quinone alkides added to crude styrene during the purification step, exhibit a synergistic polymerization inhibition effect and inhibit to a greater degree the polymerization of styrene as compared to the addition of a quinone alkide to crude styrene.

It should additionally be noted that the alkyl groups of the quinone alkides and hindered phenols, as herein described, can be increased or decreased in size thus effecting the compound molecular weight and boiling point. This is very important because the quinone alkides and hindered phenols can be made to operate at various levels in towers containing distillation sieve tower trays by changing the alkyl carbon chain length of the quinone alkides and hindered phenols.

Quinone alkides and hindered phenols which are suitable for use herein are described in the copending applications of Bacha et al, entitled "Quinone Alkide Synthesis System" U.S. Ser. No. 660,718, filed Feb. 23, 1976, and Bacha et al, entitled "Styrene Purification Process" U.S., Ser. No. 646,403, filed Jan. 2, 1976.

The following examples serve to further illustrate and instruct one skilled in the art of best mode of how to practice this invention and are not intended to be construed as limiting thereof.

EXAMPLE I

CONTROL

A 500 ml flask was charged with 300 g of styrene. A condenser connected to a vacuum system was joined to the flask, the system was flushed with dry nitrogen and the pressure reduced to 225 mm Hg. Such reduced pressure produces reflux at 105° C. The contents of the flask were heated at reflux for 3 hours; then the pressure was returned to atmospheric by the admittance of nitrogen. The contents of the flask were added to 500 ml of methanol and vigorously shaken. After standing for 0.5 hour and cooling to about 25° C., the solution was vacuum filtered to separate the methanol insoluble polymer that had formed. Traces of methanol were removed by heating (90°–100° C.) the separated polymer in a vacuum oven (315 mm Hg.) overnight. 31.5 gm of styrene polymer resulted from the isolation procedure.

EXAMPLE II

A 500 ml flask was charged with 300 gms of styrene, 0.075 gm (250 ppm) of 2,6-di-t-butyl-4-ethenyl quinone methide and 0.075 gm (250 ppm) of 2,6-di-t-butyl-4-ethyl phenol. The procedure of Example I was followed with only 1.45 gms of styrene converted to the polymer.

EXAMPLE III

The procedure described in Example I was repeated with the following exceptions: 125 ppm (.0375 gm) of 2,6-di-t-butyl-4-ethenyl quinone methide and 125 ppm (.0375 gm) of 2,6-di-t-butyl-4-methyl phenol were added to the flask. Only 4.24 gms of styrene polymerized.

EXAMPLE IV

A 500 flask was charged with 300 gms of styrene. Next, 0.075 gms (250 ppm) of 2.6-di-t-butyl-4-n-butenyl quinone methide and 0.075 gms (250 ppm) of 2.6-di-t- butyl-4-n-butyl phenol were added. The procedure of Example I was followed with only 2.93 gms of styrene polymer resulting.

EXAMPLE V

The procedure described in Example I was repeated with the following exceptions: 0.075 gms (250 ppm) of 2.6-di-t-butyl-4-sec-butenyl quinone methide and 0.075 gms (250 ppm) of 2,6-di-t-butyl-4-sec-butyl phenol were added to the flask with only 14.80 gms of styrene polymer produced.

EXAMPLE VI

A 500 ml flask was charged with 300 gms of styrene, 0.075 gms (250 ppm) of 2,6-di-t-butyl-4-isopropenyl quinone methide and .075 gms (250 ppm) of 2,6-di-t-butyl-4-isopropenyl phenol. Analysis indicated that 11.62 gms of styrene polymerized.

The results of Examples I through VI are summarized in Table I below. Table I additionally contains data from other experiments.

TABLE I

| | | STYRENE POLYMERIZATION INHIBITION* | | | | Polymer |
|---|---|---|---|---|---|---|
| Run | Styrene (gms) | Quinone Alkide[a] PPM | Hindered Phenol[b]PPM | | Time (hrs) | formed (gms) |
| 1 | 300 | None | — | None | — | 3 | 31.5 |
| 2 | 300 | None | — | BHEB | 250 | 3 | 33.6 |
| 3 | 300 | QE | 250 | None | — | 3 | 2.25 |
| 4 | 300 | QE | 250 | BHEB | 250 | 3 | 1.45 |
| 5 | 300 | QE | 125 | None | — | 3 | 8.79 |
| 6 | 300 | QE | 125 | BHT | 125 | 3 | 4.24 |
| 7 | 300 | QNB | 250 | None | — | 3 | 3.60 |
| 8 | 300 | QNB | 250 | DTBNBP | 250 | 3 | 2.93 |
| 9 | 300 | QNB | 125 | None | — | 3 | 9.86 |
| 10 | 300 | QNB | 125 | BHT | 125 | 3 | 5.73 |
| 11 | 300 | QSB | 250 | None | — | 3 | 18.23 |
| 12 | 300 | QSB | 250 | DTBSBP | 250 | 3 | 14.80 |
| 13 | 300 | QIP | 250 | None | — | 3 | 13.40 |
| 14 | 300 | QIP | 250 | DTBIPP | 250 | 3 | 11.62 |

*Each Run was conducted at 105° C. and 225 M. Hg pressure.
[a]QE = 2,6-di-t-butyl-4-ethenyl quinone methide;
QNB = 2,6-di-t-butyl-4-n-butenyl quinone methide;
QSB = 2,6-di-t-butyl-4-sec-butenyl quinone methide;
QIP = 2,6-di-t-butyl-4-isopropenyl quinone methide;
[b]BHEB = 2,6-di-t-butyl-4-ethyl phenol;
BHT = 2,6-di-t-butyl-4-methyl phenol;
DTBNBP = 2,6-di-t-butyl-4-n-butyl phenol;
DTBSBP = 2,6-di-t-butyl-4-sec-butyl phenol;
DTBIPP = 2,6-di-t-butyl-4-isopropyl phenol.

In each run above, the hindered phenol did not inhibit styrene polymerization. However, when the phenol was combined with a quinone alkide, a synergistic inhibition of styrene polymerization occurred. The phenols and quinone alkides described herein can be substituted for the phenols and quinone alkides in Table I above with substantially the same results occurring.

What is claimed is:

1. In a method for inhibiting the polymerization of styrene monomers during the vacuum distillation processing thereof, the improvement which comprises a continuous mass process for preparing styrene, adding said processing a polymerizing inhibiting amount of a quinone alkide in combination with a hindered phenol, said quinone alkide having the formula:

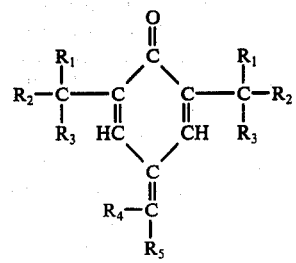

wherein $R_1$, $R_2$ and $R_3$ are either alike or different, members selected from the group consisting of hydrogen, straight or branched chain members selected from alkyl moieties having from 1 to 8 carbon atoms, phenyl and alkyl substituted phenyl moieties having up to 9 carbon atoms, cyclic hydrocarbon moieties having from 3 to 5 carbon atoms; and wherein $R_4$ and $R_5$ are either alike or different, members selected from the group consisting of hydrogen, straight or branched chain alkyl moieties having from 1 to 18 carbon atoms, phenyl and alkyl substituted phenyl moieties having 9 carbon atoms, and cyclic hydrocarbon moieties having from 3 to 5 carbon atoms; and said phenol having the formula:

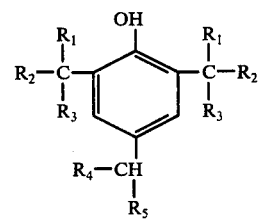

wherein $R_1$, $R_2$, $R_3$, $R_4$ and $R_5$ are defined above.

2. The method according to claim 1 wherein the quinone alkide is selected from the group of 2,6-di-t-butyl-4-methenyl quinone methide; 2,6-di-t-butyl-4-ethenyl quinone methide; 2,6-di-t-butyl-4-n-propenyl quinone methide; 2,6-di-t-butyl-4-isopropenyl quinone methide; 2,6-di-t-butyl-4-n-butenyl quinone methide; 2,6-di-t-butyl-4-iso-butenyl quinone methide; 2,6-di-t-butyl-4-sec-butenyl quinone methide; 2,6-di-t-butyl-4-n-pentenyl quinone methide; 2,6-di-t-amyl-4-methenyl quinone methide; 2,6-di-t-amyl-4-ethenyl quinone methide; 2,6-di-dodecyl-4-methenyl quinone methide; 2,6-di-n-dodecyl-4-ethenyl quinone methide; 2,6-di-cyclopentyl-4-methenyl quinone methide 2,6-di-cyclopentyl-4-ethenyl quinone methide; 2,6-di-cyclohexyl-4-methenyl quinone methide; 2,6-di-cyclohexyl-4-ethenyl quinone methide; or 2,6-di-phenyl-4-methenyl quinone methide.

3. The method according to claim 1 wherein the quinone alkide comprises from about 25 ppm to about 1,000 ppm parts of styrene.

4. The method of claim 1 wherein the hindered phenol is selected from the group of 2,6-di-t-butyl-4-methyl phenol; 2,6-di-t-butyl-4-ethyl phenol; 2,6-di-t-butyl-4-n-propyl phenol; 2,6-di-t-butyl-4-isopropyl phenol; 2,6-di-t-butyl-4-n-butyl phenol; 2,6-di-t-butyl-4-iso-butyl phenol; 2,6-di-t-butyl-4-sec-butyl phenol; 2,6-di-t-butyl-4n-pentyl phenol; 2,6-di-t-amyl-4-methyl phenol; 2,6-di-t-amyl-4-ethyl phenol; 2,6-di-n-dodecyl-4-methyl phenol; 2,6-di-n-dodecyl-4-ethyl phenol; 2,6-di-cyclo pentyl-4-methyl phenol; 2,6-di-cyclo pentyl-4-ethyl phenol; 2,6-di-cyclo hexyl-4-methyl phenol; 2,6-di-cyclo hexyl-4-ethyl phenol; or 2,6-di-phenyl-4-methyl phenol.

5. The method according to claim 1 wherein the hindered phenol comprises from about 25 ppm to about 1,000 ppm parts of styrene.

6. The method of claim 1 wherein the quinone alkide is in a molar ratio of quinone alkide to hindered phenol of from about 20:1 to about 1:10.

* * * * *